(12) United States Patent
Gelber et al.

(10) Patent No.: US 6,841,544 B2
(45) Date of Patent: Jan. 11, 2005

(54) COMPOSITION AND METHOD FOR TREATING THE EFFECTS OF DISEASES AND MALADIES

(75) Inventors: Daniel Gelber, Woodland Hills, CA (US); Richard Kleinberger, Sherman Oaks, CA (US)

(73) Assignee: Bioselect Innovations, Inc., Woodland Hills, CA (US)

( * ) Notice: Subject to any disclaimer, the term of this patent is extended or adjusted under 35 U.S.C. 154(b) by 251 days.

(21) Appl. No.: 09/754,204

(22) Filed: Jan. 5, 2001

(65) Prior Publication Data

US 2002/0006445 A1 Jan. 17, 2002

Related U.S. Application Data

(60) Provisional application No. 60/184,351, filed on Feb. 23, 2000.

(51) Int. Cl.$^7$ .............................................. A61K 31/726
(52) U.S. Cl. ............................ 514/54; 514/62; 424/725
(58) Field of Search ........................... 424/725; 514/62, 514/54

(56) References Cited

U.S. PATENT DOCUMENTS

| | | | |
|---|---|---|---|
| 2,971,844 A | 2/1961 | Bosanac | |
| 3,008,874 A | * 11/1961 | Feeney .......................... | 514/62 |
| 4,113,881 A | 9/1978 | Diehl .......................... | 424/312 |
| 4,514,421 A | 4/1985 | Herschler .................... | 514/711 |
| 4,559,329 A | 12/1985 | Herschler .................... | 514/164 |
| 4,568,547 A | 2/1986 | Herschler .................... | 514/772 |
| 4,616,039 A | 10/1986 | Herschler .................... | 514/711 |
| 4,746,675 A | 5/1988 | Makino et al. .............. | 514/423 |
| 4,826,683 A | 5/1989 | Bates .......................... | 424/641 |
| 4,973,605 A | 11/1990 | Herschler .................... | 514/708 |
| 5,011,688 A | 4/1991 | Calam et al. .............. | 424/195.1 |
| 5,021,428 A | 6/1991 | Carr et al. .................. | 514/317 |
| 5,071,878 A | 12/1991 | Herschler .................... | 514/711 |
| 5,084,482 A | 1/1992 | Hirsch et al. ............... | 514/562 |
| 5,260,073 A | 11/1993 | Phipps ........................ | 424/465 |
| 5,409,907 A | 4/1995 | Blase et al. .................. | 514/54 |
| 5,462,749 A | * 10/1995 | Rencher | |
| 5,474,757 A | 12/1995 | Yang .......................... | 514/562 |
| 5,494,668 A | * 2/1996 | Patwardhan | |
| 5,531,992 A | * 7/1996 | Yamazaki et al. | |
| 5,569,676 A | 10/1996 | Diehl .......................... | 514/549 |
| 5,571,441 A | 11/1996 | Andon et al. ................ | 252/1 |
| 5,650,157 A | 7/1997 | Bockow ...................... | 424/401 |
| 5,681,606 A | 10/1997 | Hutchison et al. .......... | 426/590 |
| 5,707,630 A | 1/1998 | Morrow ...................... | 424/195.1 |
| 5,709,855 A | 1/1998 | Bockow ...................... | 424/93.7 |
| 5,726,180 A | 3/1998 | Kurihara et al. ............ | 514/264 |
| 5,770,215 A | 6/1998 | Moshyedi .................... | 424/440 |
| 5,817,340 A | 10/1998 | Roche et al. ................ | 424/470 |
| 5,854,267 A | 12/1998 | Berlin et al. ................. | 514/370 |
| 5,871,798 A | 2/1999 | Hutchison et al. .......... | 426/590 |
| 5,888,514 A | 3/1999 | Weisman .................... | 424/195.1 |
| 5,891,465 A | 4/1999 | Keller et al. ................. | 424/450 |
| 5,932,624 A | 8/1999 | Herbert ...................... | 514/904 |
| 5,948,443 A | 9/1999 | Riley et al. .................. | 424/643 |
| 5,962,030 A | 10/1999 | Fine ............................ | 424/646 |
| 5,976,568 A | 11/1999 | Riley .......................... | 424/451 |
| 6,399,093 B1 | * 6/2002 | Petrus ........................ | 424/448 |
| 6,608,041 B2 | * 8/2003 | Hammerly ................... | 514/54 |

FOREIGN PATENT DOCUMENTS

| | | | |
|---|---|---|---|
| DE | 2103387 | * | 8/1972 |
| FR | 4804 | * | 3/1967 |
| JP | 04018022 | * | 1/1992 |
| JP | 09087174 | * | 3/1997 |

OTHER PUBLICATIONS

Campos et al., Planta Medical 55(5): 417–419 (1989). Abstract.*
Kucharz et al., Revue Roumaine de Biochimie 27(2): 145–148 (1990). Abstract.*
Muriel et al., Journal of Applied Toxicology 12(6): 439–442 (1992). Abstract.*
Wie et al. (Nutr. Res. (N. Y.) (1998), 18(1), 61–70.*

\* cited by examiner

*Primary Examiner*—Jean C. Witz
(74) *Attorney, Agent, or Firm*—Kramer & Amado, P.C.

(57) ABSTRACT

A medicinal composition for treating pain resulting from an inflammatory response comprises at least one pain relieving and anti-inflammatory pharmaceutical and at least one nutraceutical in a pharmaceutically acceptable base. The pharmaceutical is preferably acetaminophen or a non-steroidal anti-inflammatory drug (NSAID). The nutraceutical is preferably an immune booster, an anti-oxidant, a liver protectant, or a joint relief agent. Methods of using these compositions to treat pain caused by inflammation are also disclosed.

18 Claims, No Drawings

COMPOSITION AND METHOD FOR TREATING THE EFFECTS OF DISEASES AND MALADIES

This application claims the benefit of U.S. Provisional Application No. 60/184,351 entitled "Composition and Method For Treating The Effects of A Cold or Flu," filed on Feb. 23, 2000.

FIELD OF THE INVENTION

The present invention relates to the field of medicinal compositions and methods of using said compositions for treating diseases and maladies. In particular, the present invention relates to formulations comprising combinations of a pharmaceutical in combination with a nutraceutical, which when administered to a person in need thereof have the effect of increasing the beneficial effects of the pharmaceutical utilized.

BACKGROUND OF THE INVENTION

Beginning in prehistoric times, humans have attempted to treat every known type of illness and malady with naturally occurring products. Such products were initially in their natural state, such as leaves, berries, roots, tree cuttings and extracts. With the advance of science, and greater understanding of chemistry, humans have been able to synthetically produce and extract a great variety of pharmaceuticals which were previously unknown or unidentified.

With the explosion of the pharmaceutical industry in the twentieth century, controversy quickly erupted between that industry, which relied on the scientific results of its extensively tested products, and the nutraceutical industry, which had traditionally relied on less reputable sources, such as ancient herbals and verbal tradition, for its authority. Both sides have continued to develop separately due to mutual distrust of each others' practices; the natural products community being weary of the long term side-effects of man made drugs and the pharmaceutical industry disbelieving the value or efficacy of natural remedies without hard scientific proof.

Recently, the scientific community has taken an increased interest in discovering the various effects the ancient herbal remedies actually produce. Extensive studies have been conducted into the efficacy of a great number of these products and the results have largely been positive. As a result, consumers around the world have begun to take interest in these products due to the scientific data supporting the validity of their efficacy. But the greatest problem facing the average consumer of pharmaceuticals and natural remedies is the independence of both of these industries. It is often the case where a consumer purchases a natural remedy and is unaware of a pharmaceutical counterpart or vice versa. Furthermore, the benefit to consumers of products containing elements from both the nutraceutical and pharmaceutical industries could be great.

SUMMARY OF THE INVENTION

It is therefore an object of the present invention to provide formulations which combine the already know advantages of currently know pharmaceuticals along with the newly discovered benefits of nutraceuticals to produce an improved effect which not only treats a current ailment more effectively, but also functions to prevent the recurrence of illness.

It is a further object of the present invention to describe a method of treating certain maladies with pharmaceuticals, previously used for such maladies, in conjunction with the newly discovered benefits of nutraceuticals, in order to assist in the healing process as well as preventing future maladies.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel methods, arrangements, combinations, compositions and improvements herein shown and described.

In accordance with these and other objects of the invention, a brief summary of the present invention is presented. Some simplifications and omission may be made in the following summary, which is intended to highlight and introduce some aspects of the present invention, but not to limit its scope. Detailed descriptions of preferred exemplary embodiments adequate to allow those of ordinary skill in the art to make and use the invention concepts will follow in later sections.

According to a broad aspect of the invention, there is disclosed a composition for improving the efficacy of a pharmaceutical, which may include selecting a pharmaceutical used for the treatment of predetermined symptoms of an ailment and/or the ailment itself, and selecting a nutraceutical, also used for treating said predetermined symptoms of an ailment and/or the ailment itself and combining into a formulation for treating the predetermined symptoms of an ailment or the ailment itself.

In a further object of the invention, there is disclosed a method for improving the efficacy of a pharmaceutical through the selection of a pharmaceutical used for the treatment of predetermined symptoms of an ailment and/or the ailment itself and selecting a nutraceutical which is also used for treating said predetermined symptoms of an ailment and the ailment itself. The pharmaceuticals and nutraceuticals are then combined and formulated into solid, powder or liquid forms and administered to a person in need thereof.

In the present invention, there are disclosed preparations for treating the symptoms of colds, flu, allergies, or sinus discomfort as well as treating pain and discomfort associated with heartburn, general body aches, headaches, migraines, menstruation, joint discomfort and arthritis, which may include pharmaceutical ingredients, preferably selected from a group which includes, for example, acetaminophen, acetylsalicylic acid or an effective salt thereof, ibuprofen, ketoprofen, naproxen, naprosyn phenylpropanolamine bitartarate or an effective salt thereof, pseudoephedrine hydrochloride or an effective salt thereof, diphenhydramine hydrochloride or an effective salt thereof, clemastine fumarate or an effective salt thereof, chlorpheniramine maleate or an effective salt thereof, bromopheniramine maleate or an effective salt thereof, guaifenesin, dextromethorphan hydrochloride or an effective salt thereof, dextromethorphan hydrobromide or an effective salt thereof, famostidine, ranitidine, cimetidine, phenindamine tartarate or an effective salt thereof, calcium carbonate or an effective salt thereof, and combinations thereof; and nutraceutical ingredients, preferably selected from the group which includes, for example, *Echinacea purpurea, Echinacea angustifolia, Echinacea pillida, Gingko biloba*, saw palmetto, ginseng, cat's claw (uña de gato), cayenne, bilberry, cranberry, grapeseed extract, St. john's wort, cascara sagrada, valerian, elderberry, elder flower, sweet elder, *Sambucous nigra, Sambucous canadensis*, garlic, *Camellia sinensis, Camellia thea, Camellia theifera, Thea sinensis, Thea bohea, Thea viridis*, goldenseal, wild cherry (Rosacea), quercetin, stinging nettles (Urtica), curcumin, bromelain, multiple pancreatic enzymes (protease, protease II, protease m, peptidase, amylase, lipase, cellulase, maltase, lactase, invertase), *Emblica officinalis*, eicosapentaenoic acid, docosahexaeonic acid, primrose oil, feverfew, ginger root, vitamin E (D-alpha-tocopherol), licorice root (Glycyrrhiza uralensis), aloe vera, horseradish root, L-glutamine, ascorbic acid, antiscorbutic vitamin, rose hips, calcium ascorbate, cevitamic acid, citrus bioflavonoids complex, acerola, zinc or an effective salt thereof, *Astragalus membranaceous, Astragalus mongolicus*, membranous milk vetch, milk vetch, mongolian milk, dong quai, huangqi, hunag qi, moringa and combinations thereof. Although these ingredients are preferred, other pharmaceuticals and nutraceuticals may be substituted in their place.

According to another broad aspect of the invention, a method is disclosed for treating the symptoms of colds, flu, allergies, or sinus discomfort as well as treating pain and discomfort associated with heartburn, general body aches, headaches, migraines, menstruation, joint discomfort and arthritis which includes formulating a composition which may include pharmaceutical ingredients preferably selected, for example, from a group which includes, acetaminophen, acetylsalicylic acid or an effective salt thereof, ibuprofen, ketoprofen, naproxen, naprosyn phenylpropanolamine bitartarate or an effective salt thereof, pseudoephedrine hydrochloride or an effective salt thereof, diphenhydramine hydrochloride or an effective salt thereof, clemastine fumarate or an effective salt thereof, chlorpheniramine maleate or an effective salt thereof, bromopheniramine maleate or an effective salt thereof, guaifenesin, dextromethorphan hydrochloride or an effective salt thereof, dextromorphan hydrobromide or an effective salt thereof, famostidine, ranitidine, dimetidine, phenindamine tartarate or an effective salt thereof, calcium carbonate or an effective salt thereof, and combinations thereof, and nutraceutical ingredients, preferably selected, for example, from a group which includes, *Echinacea purpurea, Echinacea angustifolia, Echinacea pillida, Gingko biloba*, saw palmetto, ginseng, cat's claw (u na de gato), cayenne, bilberry, cranberry, grapeseed extract, St. john's wort, cascara sagrada, valerian, elderberry, elder flower, sweet elder, *Sambucous nigra, Sambucous canadensis*, garlic, *Camellia sinensis, Camellia thea, Camellia theifera, Thea sinensis, Thea bohea, Thea viridis*, goldenseal, wild cherry (Rosacea), quercetin, stinging nettles (Urtica), curcumin, bromelain, multiple pancreatic enzymes (protease, protease II, protease III, peptidase, amylase, lipase, cellulase, maltase, lactase, invertase), *Emblica officinalis*, eicosapentaenoic acid, docosahexaeonic acid, primrose oil, feverfew, ginger root, vitamin E (D-alpha-tocopherol), licorice root (*Glycyrrhiza uralensis*), aloe vera, horseradish root, L-glutamine, natural marine lipid concentrate, ascorbic acid, antiscorbutic vitamin, rose hips, calcium ascorbate, cevitamic acid, citrus bioflavonoids complex, acerola, zinc or an effective salt thereof, *Astragalus membranaceous, Astragalus mongolicus*, membranous milk vetch, milk vetch, mongolian milk, dong quai, huangqi, hunag qi, moringa and combinations thereof.

The formulation containing a pharmaceutical ingredient and a nutraceutical ingredient is then administered in order to remedy one of the above-referenced maladies. Although these ingredients are preferred, other pharmaceutical and nutraceutical ingredients may be substituted in their place.

DETAILED DESCRIPTION OF THE PREFERRED EMBODIMENTS OF THE INVENTION

For the purposes of this specification, the word "pharmaceutical" refers to a material that is:

a) a synthetically produced bioactive compound, where no structurally identical, naturally produced analog to the synthetically produced bioactive compound exists; or b) a biologically active compound derived from a living organism, where the biologically active compound is not a dietary supplement.

The pharmaceuticals utilized in this invention include the equivalent and alternative salts which may be formulated from the base pharmaceuticals and which achieve substantially the same effect as the pharmaceutical listed.

For the purposes of this specification, a "dietary supplement" is defined as a product (other than tobacco) that bears or contains one or more of the following dietary ingredients: a vitamin, a mineral, an herb or other botanical, an amino acid, a dietary substance for use by man to supplement the diet by increasing the total daily intake of that substance, or a concentrate, metabolite, constituent, extract, or combinations of these ingredients.

The word "nutraceutical," for the purposes of this specification, refers to a food item, or a part of a food item, that offers medical health benefits, including prevention and/or treatment of disease. More particularly, a nutraceutical is a material that is:

a) a dietary supplement containing a nutritive bioactive compound; or b) a biologically active processed or unprocessed material derived from a plant, a fungus, an animal, or a portion thereof; where the precise composition of the biologically active processed or unprocessed material may be undetermined.

Examples of a biologically active processed material may include a finely chopped, powdered, pureed, or cooked material derived from plant or animal tissue, or an extract of plant or animal tissue.

Broadly, the inventive composition is a medicinal composition containing a pharmaceutical used for the treatment of a first predetermined ailment or a symptom thereof, and a nutraceutical used for treatment of a second predetermined ailment or a symptom thereof. The pharmaceutical and the nutraceutical are mixed and compounded with a pharmaceutically acceptable base into a pharmaceutical dosage form.

The preferred pharmaceuticals include pain relieving and/or anti-inflammatory drugs, such as acetaminophen, non-steroidal anti-inflammatory drugs, and mixtures thereof. These non-steroidal anti-inflammatory drugs include diclophenac, fenflofenac; aspirin; indomethacin, sulindac, tolmetin, ibuprofen, ketoprofen, fenoprofen, flurbiprofen, naproxen, meclofenamic acid, flufenamic acid, piroxicam, tenoxicam, meloxicam, celicoxib, roficoxib, nabumetone, effective salts thereof, derivatives thereof, and combinations thereof.

A second class of pharmaceuticals which may be used is the antihistamines. The antihistamines include astemizole, azatadine, brompheniramine, cetirizine, chlorpheniramine, clemastine, cyproheptadine, dexchlorpheniramine, dimenhydrinate, diphenhydramine, doxylamine, hydroxyzine, loratadine, phenindamine, terfenadine, tripelennamine, effective salts thereof, derivatives thereof, and mixtures thereof, with diphenhydramine and chlorpheniramine being particularly preferred.

A third class of pharmaceuticals which may be used is the decongestants. Particularly preferred decongestants include ephedrine, phenylephrine, phenylpropanolamine and pseudoephedrine, effective salts thereof, derivatives thereof, and mixtures thereof. The decongestants are commonly used in combination with antihistamines.

Pharmaceuticals for use in treating acid reflux disease or gastric ulcers may be used as a fourth class of drugs. The Histamine $H_2$-receptor antagonists Cimetidine, Famotidine, Nizatidine, and Ranitidine are particularly useful for this purpose.

Expectorants such as Guaifenesin are also acceptable pharmaceuticals, as are cough suppressants such as dextromethorphan.

The therapeutic uses of the pharmaceuticals used in the present invention are well known and need no further explanation. The nutraceuticals which may be used in the present invention have a variety of medicinal uses which improve the efficacy of pharmaceuticals.

The immune boosters and/or anti-viral agents are a first class of nutraceuticals. These agents are useful for accelerating wound-healing and improved immune function; and they include extracts from the coneflowers, or herbs of the genus *Echinacea*, such as *Echinacea purpurea, Echinacea angustfolia, Echinacea pillida*, and mixtures thereof; extracts from herbs of the genus Sambuca, such as elderberries; and Goldenseal extracts. The coneflowers in particular are a popular herbal remedy used in the central United States, an area to which they are indigenous. The coneflowers normally contain about 0.1% of echinacoside, a caffeic acid glycoside, and echinacein, a complex isobutylamide. The extract derived from the roots contains varying amounts of unsaturated alkyl ketones or isobutylamides. Goldenseal is an immune booster with antibiotic activity, and includes the compounds berberine and hydrastine, which respectively stimulate bile secretions and constrict peripheral blood vessels. *Astragalus membranaceous, Astragalus mongolicus*, and other herbs of the genus *Astragalus* are also effective immune boosters in either their natural or processed forms. *Astragalus* stimulates development into of stem cells in the marrow and lymph tissue active immune cells. Zinc and its bioactive salts, such as zinc gluconate and zinc acetate, also act as immune boosters in the treatment of the common cold.

Antioxidants are a second class of nutraceuticals. These antioxidants include the natural, sulfur-containing amino acid allicin, which acts to increase the level of antioxidant enzymes in the blood. Herbs or herbal extracts, such as garlic, which contain allicin are also effective antioxidants. The catechins, and the extracts of herbs such as green tea containing catechins, are also effective antioxidants. Extracts of the immune boosters *Astragalus membranaceous, Astragalus mongolicus*, and other herbs of the genus *Astragalus* also show antioxidant activity. The bioflavonoids, such as quercetin, hesperidin, rutin, and mixtures thereof, are also effective as antioxidants. The primary beneficial role of the bioflavonoids may be in protecting vitamin C from oxidation in the body. This makes more vitamin C, or ascorbic acid, available for use by the body. Ascorbic acid, which is itself an important antioxidant nutraceutical, functions as a free radical scavenger that helps reduce oxidative stress and/or cell damage caused by free radicals.

Bioflavonoids such as quercetin are also effective anti-inflammatory agents, and may be used as such in the inventive compositions. Anti-inflammatory herbal nutraceuticals and anti-inflammatory nutraceutical compounds derived from plants or herbs may also be used as anti-inflammatory agents in the inventive composition. These include bromolain, a proteolytic enzyme found in pineapple; teas and extracts of stinging nettle; turmeric, extracts of turmeric, or curcumin, a yellow pigment isolated from turmeric.

Liver protectants are also effective nutraceuticals which may be used in this invention. Silymarin, an extract from milk thistle seeds containing three isomeric flavonolignans, is a particularly effective liver protectant, and is useful in treatment of patients with AIDS. Milk thistle and its extracts also appear to exhibit some antioxidant activity.

Another nutraceutical which is used in the present invention is ginger, derived from herbs of the genus *Zingiber*, such as *Zingiber officinale, Zingiber capitatum* and *Zingiber zerumbet*. This nutraceutical has been found to possess cardiotonic activity due to compounds such as gingerol and the related compound shogaol as well as providing benefits in the treatment of dizziness, and vestibular disorders. Ginger is also effective in the treatment of nausea and other stomach disorders.

Other nutraceuticals effective against stomach disorders are licorice and its extracts, and aloe vera. Licorice stimulates the bile production by the liver, and can relieve ulcers and stomach aches and lower cholesterol. Studies on animals indicate that aloe vera and extracts or juices prepared therefrom help maintain a healthy stomach lining and assist in digestion. L-glutamine is also effective in treating digestive disorders, as are juices containing L-glutamine. L-Glutamine helps protect the structural integrity of the bowels, making it useful for treating ulcers and "leaky gut syndrome."

Nutraceuticals which assist in rebuilding soft tissue structures, particularly in rebuilding cartilage, are useful in compositions for treating the pain of arthritis and other joint disorders. Glucosamine, glucosamine sulfate, chondroitin, and chondroitin sulfate are particularly useful for this purpose. Chondroitin may be derived from a variety of sources, such as Elk Velvet Antler. Marine lipid complexes, omega 3 fatty acid complexes, and fish oil are also known to be useful in treating pain associated with arthritis.

Nutraceuticals useful in treating migraine headaches include feverfew and *Gingko biloba*. The main active ingredient in feverfew is the sesquiterpene lactone parthenolide, which inhibits the secretion of prostaglandins which in turn cause pain through vasospastic activity in the blood vessels. Feverfew also exhibits anti-inflammatory properties. Fish oil, owing to its platelet-stabilizing and antivasospastic actions, may also be useful in treating migraine headaches. The herb *Gingko biloba* also assists in treatment of migraines by stabilizing arteries and improving blood circulation.

Wild cherry bark extracts have a sedative action on the cough reflex, making them effective nutraceutical components of cough suppressant formulations. Additionally, they are effective at soothing sore throat pain.

Although some of the sample nutraceuticals listed above have been described as to their pharmacological effects, other nutraceuticals may also be utilized in the present invention and their effects are well documented in the scientific literature.

In a first embodiment, the medicinal compositions described herein are effective in treating ailments or symptoms thereof which are caused by immune responses. These immune responses may be responses to viruses; microorganisms such as bacteria; and allergens such as molds, spores, pet dander, atmospheric pollutants, and chemical compounds. The ailments which exhibit these immune responses as symptoms include colds and the flu. The symptoms of these immune responses include headaches, body aches, fever, nasal and/or sinus congestion, coughing, and general fatigue. The composition includes a pharmaceutical and a nutraceutical, each of which is effective against at least one ailment or a symptom thereof, where the ailment or the symptom is caused by an immune response. The pharmaceutical and the nutraceutical may treat the same or different symptoms. In a first aspect of this embodiment, an effective medication for treating a cold, the flu, or a related symptom may be prepared by combining at least one of the pain-relieving and/or anti-inflammatory, antihistaminic, and/or decongestant pharmaceuticals listed in Table 1 with at least one of the immune-boosting, antioxidant, and/or liver protective nutraceuticals listed in Table 1, and compounding them into a pharmaceutically acceptable dosage form.

TABLE 1

Preferred Ingredients of Pharmaceutical/Nutraceutical Formulations for Treating a Cold or the Flu

| Pain-Relieving and or Anti-inflammatory Pharmaceuticals | Immune boosting and/or Anti-Viral Nutraceuticals |
|---|---|
| Acetaminophen | Coneflower extracts |
| Non-Steroidal Anti-inflammatory drugs | Elderberry extracts |
| Antihistaminic Pharmaceuticals | Goldenseal extracts |
| Diphenhydramine | Zinc gluconate |
| Chlorpheniramine | Zinc acetate |
| Astemizole | Zinc oxide |
| Azatadine | Antioxidant Nutraceuticals |
| Cetirizine | Garlic and its extracts |
| Clemastine | Green tea and its extracts |
| Cyproheptadine | Astragalus extracts |
| Loratadine | Grapefruit seed extracts |
| Terfenadine | Vitamin C |
| Decongestant Pharmaceuticals | Allicin |
| Ephedrine | Catechins |
| Phenylephrine | Bioflavonoids |
| Phenylpropanolamine | Liver Protectant Nutraceuticals |
| Pseudoephedrine | Milk Thistle extracts |

Particularly preferred formulations in accordance with the first embodiment of the invention include pharmaceutical dosage forms effective against cold and/or flu which contain:

a) a pain-relieving and/or anti-inflammatory pharmaceutical agent in combination with at least one nutraceutical selected from the group consisting of immune boosters and/or anti-viral agents, antioxidants, and the liver protectant milk thistle;

b) an antihistaminic pharmaceutical agent in combination with at least one nutraceutical selected from the group consisting of immune boosters and/or anti-viral agents and antioxidants;

c) a decongestant pharmaceutical agent in combination with at least one nutraceutical selected from the group consisting of immune boosters and/or anti-viral agents and antioxidants;

d) a mixture of a pain-relieving and/or anti-inflammatory pharmaceutical agent and an antihistaminic pharmaceutical agent in combination with at least one nutraceutical selected from the group consisting of immune boosters and/or anti-viral agents, antioxidants, and the liver protectant milk thistle;

e) a mixture of a pain-relieving and/or anti-inflammatory pharmaceutical agent and a decongestant pharmaceutical agent in combination with at least one nutraceutical selected from the group consisting of immune boosters and/or anti-viral agents, antioxidants, and the liver protectant milk thistle;

f) a mixture of a decongestant pharmaceutical agent and an antihistaminic pharmaceutical agent in combination with at least one nutraceutical selected from the group consisting of immune boosters and/or anti-viral agents, anti-inflammatory nutraceuticals, and antioxidants; and g) a mixture of a pain-relieving and/or anti-inflammatory pharmaceutical agent, a decongestant pharmaceutical agent, and an antihistaminic pharmaceutical agent in combination with at least one nutraceutical selected from the group consisting of immune boosters and/or anti-viral agents, antioxidants, and the liver protectant milk thistle.

It is also possible to add a pain-relieving and anti-inflammatory nutraceutical to the above compositions.

Preferably, the liver protectant milk thistle is only used as a nutraceutical in compositions containing a pain-relieving and/or anti-inflammatory pharmaceutical agent or an antihistamine; more preferably, the liver protectant milk thistle is used as a nutraceutical in compositions containing acetaminophen or an antihistamine.

In a second aspect of the first embodiment, the invention relates to a pharmaceutical composition for treating immune responses resulting from exposure to atmospheric pollutants or allergens. The symptoms of these immune responses include sinus congestion; red, itchy, or watery eyes; and sneezing. An effective medication for treating allergies or sinus conditions may be prepared by combining at least one of the antihistaminic pharmaceuticals and/or decongestant pharmaceuticals listed in Table 2 with at least one of the anti-inflammatory, antioxidant, and/or liver protective nutraceuticals listed in Table 2, and compounding them into a pharmaceutically acceptable dosage form.

TABLE 2

Preferred Ingredients of Pharmaceutical/Nutraceutical Formulations for Treating Allergies and/or Sinus Conditions

| Decongestant Pharmaceuticals | Anti-inflammatory Nutraceuticals |
|---|---|
| Ephedrine | Bioflavonoids |
| Phenylephrine | Curcumin |
| Phenylpropanolamine | Quercetin |
| Pseudoephedrine | Stinging nettle extracts |
| Antihistaminic Pharmaceuticals | Turmeric and its extracts |
| Diphenhydramine | Bromolain |
| Chlorpheniramine | Antioxidant Nutraceuticals |
| Astemizole | Garlic and its extracts |
| Azatadine | Green tea and its extracts |
| Cetirizine | Astragalus extracts |
| Clemastine | Grapefruit seed extracts |
| Cyproheptadine | Vitamin C |
| Loratadine | Allicin |
| Terfenadine | Catechins |
|  | Bioflavonoids |
|  | Liver Protectant Nutraceuticals |
|  | Milk Thistle extracts |

Particularly preferred formulations in accordance with this aspect of the invention include pharmaceutical dosage forms for treating allergy and sinus conditions which contain:

a) a decongestant agent in combination with at least one nutraceutical selected from the group consisting of anti-inflammatories, anti-oxidants and liver protectants;

b) an antihistamine agent in combination with at least one nutraceutical selected from the group consisting of anti-inflammatories, anti-oxidants and liver protectants; or c) a mixture of a decongestant agent and an antihistamine agent in combination with at least one nutraceutical selected from the group consisting of anti-inflammatories, anti-oxidants and liver protectants.

In a second embodiment, the invention relates to a pharmaceutical composition for immune responses of the respiratory system, or symptoms thereof. These immune responses can cause coughing reflexes and accumulation of mucous in the throat and/or respiratory system. An effective medication for treating coughs may be prepared by combining at least one of the cough suppressant pharmaceuticals listed in Table 3 with at least one of the immune-boosting, antioxidant, cough reflex sedative, and/or liver protective nutraceuticals listed in Table 3, and compounding them into a pharmaceutically acceptable dosage form. A decongestant or expectorant pharmaceutical listed in Table 3 may optionally be present in the cough medication for treating accumulation of mucous. It is also possible to prepare an effective cough medication containing a decongestant pharmaceutical with no cough suppressant or expectorant pharmaceuticals present, if a cough reflex sedative such as wild cherry bark extract is included in the formulation. An effective medication for treating an accumulation of mucous may be prepared by combining an expectorant and/or a decongestant with a nutraceutical listed in Table 3.

TABLE 3

Preferred Ingredients of
Pharmaceutical/Nutraceutical Formulations for Treating
Respiratory Immune Responses

| Cough Suppressant Pharmaceuticals | Immune boosting and/or |
|---|---|
| Dextromethorphan | Anti-Viral Nutraceuticals |
| Expectorant Pharmaceuticals | Coneflower extracts |
| Guaifenesin | Elderberry extracts |
| Decongestant Pharmaceuticals | Goldenseal extracts |
| Ephedrine | Zinc gluconate |
| Phenylephrine | Zinc acetate |
| Phenylpropanolamine | Zinc oxide |
| Pseudoephedrine | Antioxidant Nutraceuticals |
| | Garlic and its extracts |
| | Green tea and its extracts |
| | Astragalus extracts |
| | Grapefruit seed extracts |
| | Vitamin C |
| | Allicin |
| | Catechins |
| | Bioflavonoids |
| | Liver Protectant Nutraceuticals |
| | Milk Thistle Extracts |
| | Nutraceuticals for Sedating the Cough Reflex |
| | Wild Cherry Extract |

Particularly preferred formulations, in accordance with the second embodiment of the invention, include pharmaceutical dosage forms for treating respiratory immune responses and which comprise the following:

a) a cough suppressing pharmaceutical agent in combination with at least one nutraceutical selected from the group consisting of immune boosters and/or anti-viral agents, anti-oxidants and cough reflex sedatives;

b) an expectorant pharmaceutical agent in combination with at least one nutraceutical selected from the group consisting of immune boosters and/or anti-viral agents, anti-oxidants and cough reflex sedatives;

c) a mixture of a cough suppressing pharmaceutical agent and an expectorant pharmaceutical agent in combination with at least one nutraceutical selected from the group consisting of immune boosters and/or anti-viral agents, anti-oxidants and cough reflex sedatives;

d) a mixture of a cough suppressing pharmaceutical agent and a decongestant pharmaceutical agent in combination with at least one nutraceutical selected from the group consisting of immune boosters and/or anti-viral agents, anti-oxidants and cough reflex sedatives;

e) a mixture of an expectorant pharmaceutical agent and a decongestant pharmaceutical agent in combination with at least one nutraceutical selected from the group consisting of immune boosters and/or anti-viral agents, anti-oxidants and cough reflex sedatives;

f) a mixture of a cough suppressing pharmaceutical agent, an expectorant pharmaceutical agent, and a decongestant pharmaceutical agent in combination with at least one nutraceutical selected from the group consisting of immune boosters and/or anti-viral agents, anti-oxidants and cough reflex sedatives; or g) a decongestant, a nutraceutical which acts as a cough reflex sedative, and optionally at least one nutraceutical selected from the group consisting of immune boosters and/or anti-viral agents, and anti-oxidants.

In a third embodiment, the invention relates to an analgesic pharmaceutical composition for treating pain brought about by an inflammatory response. An effective medication for treating pain conditions may be prepared by combining at least one of the pain-relieving and/or anti-inflammatory pharmaceutical agents listed in Table 4 with at least one of the immune-booster and/or anti-viral nutraceuticals, antioxidant nutraceuticals, joint relief nutraceuticals and liver protectant nutraceuticals listed in Table 4, and compounding them into a pharmaceutically acceptable dosage form.

TABLE 4

Preferred Ingredients of Analgesic and/or Pain Relieving
Pharmaceutical/Nutraceutical Formulations

| Pain-Relieving and/or Anti-inflammatory Pharmaceuticals | Immune boosting and/or Anti-Viral Nutraceuticals |
|---|---|
| Acetaminophen | Coneflower extracts |
| diclophenac | Elderberry extracts |
| fenflofenac | Goldenseal extracts |
| aspirin | Zinc gluconate |
| indomethacin | Zinc acetate |
| sulindac | Zinc oxide |
| tolmetin | Antioxidant Nutraceuticals |
| ibuprofen | Garlic and its extracts |
| ketoprofen | Green tea and its extracts |
| fenoprofen | Astragalus extracts |
| flurbiprofen | Grapefruit seed extracts |
| naproxen | Vitamin C |
| meclofenamic acid | Allicin |
| flufenamic acid | Catechins |
| piroxicam | Bioflavonoids |
| tenoxicam | Liver Protectant Nutraceuticals |
| meloxicam | Milk Thistle Extracts |
| celicoxib | Nutraceuticals for relief of |
| roficoxib | Joint Pain |
| nabumetone | Glucosamine sulfate |
| | Chondroitin sulfate |

In a fourth embodiment, the invention relates to an pharmaceutical composition for relieving migraine pain. An effective medication for treating pain conditions may be prepared by combining at least one of the pain-relieving and/or anti-inflammatory pharmaceutical agents listed in Table 5 with at least one of the vascular dilating nutraceuticals, anti-nausea nutraceuticals, and liver protectant nutraceuticals listed in Table 5, and compounding them into a pharmaceutically acceptable dosage form.

TABLE 5

Preferred Ingredients of Pharmaceutical/Nutraceutical Formulations for Treating Migraine Headaches

| Pain-Relieving and/or Anti-inflammatory Pharmaceuticals | Nutraceutical Vascular Dilators |
|---|---|
| | Feverfew and its extracts |
| Acetaminophen | Gingko biloba and its extracts |
| diclophenac | Omega 3 fatty acid complexes |
| fenflofenac | Marine Lipid Complex |
| aspirin | Anti-nausea Nutraceuticals |
| indomethacin | Ginger and its extracts |
| sulindac | Liver Protectant |
| tolmetin | Nutraceuticals |
| ibuprofen | Milk Thistle extracts |
| ketoprofen | |
| fenoprofen | |
| flurbiprofen | |
| naproxen | |
| meclofenamic acid | |
| flufenamic acid | |
| piroxicam | |
| tenoxicam | |
| meloxicam | |
| celicoxib | |
| roficoxib | |
| nabumetone | |

In a fifth embodiment, the invention relates to an pharmaceutical composition for treating acid reflux disease and/or heartburn. An effective medication for treating acid reflux may be prepared by combining at least one of the pharmaceutical agents listed in Table 6 with at least one of the nutraceuticals for treating stomach disorders and/or protecting the integrity of the gut or protecting the liver listed in Table 6, and compounding them into a pharmaceutically acceptable dosage form.

TABLE 6

Preferred Ingredients of Pharmaceutical/Nutraceutical Formulations for Treating Acid Reflux Disease

| Acid-controlling Pharmaceuticals | Nutraceuticals Useful for Soothing Stomach Disorders |
|---|---|
| Cimetidine | |
| Famotidine | Ginger and its extracts |
| Nizatidine | Licorice and its extracts |
| Ranitidine | Aloe vera |
| | Nutraceuticals Useful for Protecting the Gastric Mucosal Lining |
| | L-Glutamine |
| | Liver Protectant Nutraceuticals |
| | Milk Thistle extracts |

Formulations of the first five embodiments of the invention may be prepared in accordance with compounding standards commonly know in the art and further described in the "Pharmaceutical Manufacturing Encyclopedia" by Marshall Sittig (Noyes Publications, $2^{nd}$ Edition, 1988), hereby incorporated herein by reference. The invention also encompasses the addition of one or more pharmaceutical additives commonly used in the formulation of pharmaceuticals and nutritional supplements as set forth in the "Handbook of Pharmaceutical Additives" by Michael Ash and Irene Ash (Gower Publishing, Limited, 1995), hereby incorporated herein by reference. Such additives comprise excipients, adjuvants, solvents, carriers, flavorants, stabilizers, binders and coatings. These allow for the formulation of the various embodiments into tablets; capsules; orally-administered or injectable liquids, suspensions, or dispersions; powders; and suppositories.

In a sixth embodiment, the invention relates to a nasal decongestant spray. An effective medication for treating nasal congestion may be prepared by combining at least one of the decongestant pharmaceutical agents listed in Table 7 with at least one of the immune-boosting and or antioxidant nutraceuticals listed in Table 7, and combining them with a liquid vehicle. Preferably, the decongestant and the nutraceutical are dissolved or dispersed into an aqueous saline solution. The solution is then packaged as a spray, which can be administered topically onto the nasal mucosa.

TABLE 7

Preferred Ingredients of Pharmaceutical/Nutraceutical Formulations for Use in Nasal Decongestant Sprays

| Decongestant Pharmaceuticals | Immune Boosting and/or Anti-Viral Nutraceuticals |
|---|---|
| Ephedrine | |
| Phenylephrine | Coneflower extracts |
| Phenylpropanolamine | Elderberry extracts |
| Pseudoephedrine | Goldenseal extracts |
| | Zinc gluconate |
| | Zinc acetate |
| | Zinc oxide |
| | Antioxidant Nutraceuticals |
| | Garlic and its extracts |
| | Green tea and its extracts |
| | Astragalus extracts |
| | Vitamin C |
| | Allicin |
| | Catechins |
| | Bioflavonoids |

The following examples constitute some of the embodiments of the invention as well as the preferred embodiments and the most preferred embodiments. The active ingredients specified in the illustrative embodiments are stated in ranges which are suitable for carrying out the invention.

Examples of formulations which demonstrate the present invention in some of its embodiments are provided below. Unless otherwise stated, herbal ingredients are used in the form of dried extracts.

EXAMPLE 1

A solid composition comprising, Acetaminophen, in a range of approximately 60 mg to 1000 mg, in a preferred range of approximately 200 mg to 750 mg, and in a most preferred range of approximately 350 mg to 550 mg, Diphenhydramine in a range of approximately 5 mg to 100 mg, in a preferred range of approximately 10 mg to 50 mg, and in a most preferred range of approximately 20 mg to 40 mg, Pseudoephedrine in a range of approximately 5 mg to 100 mg, in a preferred range of approximately 10 mg to 75 mg, and in a most preferred range of approximately 20 mg to 40 mg, *Echinacea purpurea* in a range of approximately 10 mg to 500 mg, in a preferred range of approximately 25 mg to 200 mg, and in a most preferred range of approximately 50 mg to 100 mg, Goldenseal in a range of approximately 50 mg to 200 mg, in a preferred range of approximately 75 mg to 150 mg, and in a most preferred range of approximately 80 mg to 120 mg, Elderberry (sambucol) in a range of approximately 50 mg to 250 mg, in a preferred range of approximately 75 mg to 175 mg, and in a most preferred range of approximately 100 mg to 150 mg, Garlic extract in a range of approximately 50 mg to 200 mg, in a preferred range of approximately 75 mg to 150 mg, and in a most preferred range of approximately 80 mg to 120 mg, Green tea extract in a range of approximately 50 mg to 200 mg, in a preferred range of approximately 75 mg to 150 mg, and in a most preferred range of approximately 80 mg to 120 mg, *Astragalus* in a range of approximately 50 mg to 250 mg, in a preferred range of approximately 75 mg to 175 mg, and in a most preferred range of approximately 100 mg to 150 mg, Zinc gluconate in a range of approximately 0.1 mg to 15 mg, in a preferred range of approximately 0.5 mg to 10 mg, and in a most preferred range of approximately 1 mg to 7.5 mg, and Ascorbic acid in a range of approximately 50 mg to 1000 mg, in a preferred range of approximately 100 mg to 750 mg, and in a most preferred range of approximately 200 mg to 500 mg. This composition is administered to a mammal, in need thereof, in the form of a capsule, for treating the symptoms of a cold or flu every 4 to 6 hours to relieve pain and discomfort associated with a cold or flu and to provide immune system stimulation. *Echinacea purpurea* and *Astragalus* assist in boosting the immune system while the pharmaceutical components treat the symptoms associated with inflammatory responses and mucous accumulation.

EXAMPLE 2

A composition comprising, Ibuprofen in a range of approximately 50 mg to 500 mg, in a preferred range of approximately 100 mg to 350 mg, and in a most preferred range of approximately 125 mg to 250 mg, Chlorpheniramine in a range of approximately 0.1 mg to 10 mg, in a preferred range of approximately 0.5 mg to 7.5 mg, and in a most preferred range of approximately 1 mg to 3 mg, Pseudoephedrine in a range of approximately 5 mg to 100 mg, in a preferred range of approximately 10 mg to 75 mg, and in a most preferred range of approximately 20 mg to 50 mg, *Echinacea purpurea* in a range of approximately 10 mg to 500 mg, in a preferred range of approximately 25 mg to 200 mg, and in a most preferred range of approximately 50 mg to 100 mg, Goldenseal in a range of approximately 50 mg to 200 mg, in a preferred range of approximately 75 mg to 150 mg, and in a most preferred range of approximately 80 mg to 120 mg, Elderberry (sambucol) in a range of approximately 50 mg to 250 mg, in a preferred range of approximately 75 mg to 175 mg, and in a most preferred range of approximately 100 mg to 150 mg, Garlic extract in a range of approximately 50 mg to 200 mg, in a preferred range of approximately 75 mg to 150 mg, and in a most preferred range of approximately 80 mg to 120 mg, Green tea extract in a range of approximately 50 mg to 200 mg, in a preferred range of approximately 75 mg to 150 mg, and in a most preferred range of approximately 80 mg to 120 mg, *Astragalus* in a range of approximately 50 mg to 250 mg, in a preferred range of approximately 75 mg to 175 mg, and in a most preferred range of approximately 100 mg to 150 mg, Zinc gluconate in a range of approximately 0.1 mg to 15 mg, in a preferred range of approximately 0.5 mg to 10 mg, and in a most preferred range of approximately 1 mg to 7.5 mg, and Ascorbic acid in a range of approximately 50 mg to 1000 mg, in a preferred range of approximately 100 mg to 750 mg, and in a most preferred range of approximately 200 mg to 500 mg. This composition is administered to a mammal, in a liquid form, for treating the symptoms of a cold or flu every 4 to 6 hours to relieve pain and discomfort associated with a cold or flu and to provide immune system stimulation.

EXAMPLE 3

A composition comprising, Aspirin, in an approximate range of 80 mg to 1000 mg, Pseudoephedrine HCl, in an approximate range of 2.5 mg to 240 mg, Diphenhydramine HCl, in an approximate range of 6.25 mg to 1000 mg, an herb selected from the genus Echinacea, in an approximate range of 100 mg to 1000 mg, Elderberry, in approximate range of 50 mg to 500 mg, Green tea, in an approximate range of 100 mg to 400 mg, vitamin C, in an approximate range of 45 mg to 1000 mg, Zinc, in an approximate range of 10 mg to 50 mg, and *Astragalus*, in an approximate range of 500 mg to 1000 mg, are administered to a mammal, for treating the aches, pains and discomfort associated with a cold or flu as well as boosting the immune system.

EXAMPLE 4

A liquid composition comprising Guaifenesin in a range of approximately 25 mg to 250 mg, in a preferred range of approximately 50 mg to 175 mg, and in a most preferred range of approximately 75 mg to 150 mg, Phenylpropanolamine hydrochloride in a range of approximately 2 mg to 25 mg, in a preferred range of approximately 5 mg to 20 mg, and in a most preferred range of approximately 7.5 mg to 15 mg, Dextromethorphan hydrochloride in a range of approximately 1 mg to 20 mg, in a preferred range of approximately 5 mg to 15 mg, and in a most preferred range of approximately 7.5 mg to 12.5 mg, *Echinacea purpurea* in a range of approximately 50 mg to 500 mg, in a preferred range of approximately 100 mg to 350 mg, and in a most preferred range of approximately 150 mg to 275 mg, Elderberry in a range of approximately 10 mg to 250 mg, in a preferred range of approximately 25 mg to 200 mg, and in a most preferred range of approximately 75 mg to 175 mg, Ascorbic acid in a range of approximately 50 mg to 1000 mg, in a preferred range of approximately 100 mg to 750 mg, and in a most preferred range of approximately 200 mg to 500 mg, wild cherry bark in a range of approximately 0.1 mg to 50 mg, in a preferred range of approximately 0.5 mg to 25 mg, and in a most preferred range of approximately 1 mg to 15 mg, and milk thistle in a range of approximately 10 mg to 100 mg, in a preferred range of approximately 20 mg to 75 mg, and in a most preferred range of approximately 40 mg to 60 mg, is administered to a person in need thereof in liquid form ranging from 2.5 ml to 10 ml, up to four times daily, for treating coughing symptoms and having an expectorant effect.

EXAMPLE 5

A composition comprising Phenylpropanolamine hydrochloride in a range of approximately 2 mg to 25 mg, in a preferred range of approximately 5 mg to 20 mg, and in a most preferred range of approximately 6.5 mg to 15 mg, Dextromethorphan hydrochloride in a range of approximately 1 mg to 20 mg, in a preferred range of approximately 2.5 mg to 15 mg, and in a most preferred range of approximately 5 mg to 10 mg, *Echinacea purpurea* in a range of approximately 1 mg to 100 mg, in a preferred range of approximately 2.5 mg to 50 mg, and in a most preferred range of approximately 5 mg to 25 mg, Elderberry in a range of approximately 10 mg to 150 mg, in a preferred range of approximately 25 mg to 125 mg, and in a most preferred range of approximately 50 mg to 100 mg, ascorbic acid in a range of approximately 50 mg to 1000 mg, in a preferred range of approximately 75 mg to 500 mg, and in a most preferred range of approximately 100 mg to 250 mg, and Wild cherry in a range of approximately 0.1 mg to 50 mg, in a preferred range of approximately 0.5 mg to 25 mg, and in a most preferred range of approximately 1 mg to 15 mg, is administered to a person in need thereof in liquid form, at a dosage of between 2.5 ml to 10 ml, up to four time daily for treating coughing symptoms and having an expectorant effect.

EXAMPLE 6

A composition comprising Pseudoephedrine sulfate in a range of approximately 10 mg to 100 mg, in a preferred range of approximately 15 mg to 75 mg, and in a most preferred range of approximately 25 mg to 50 mg, Chlorphenriamine sulfate in a range of approximately 0.5 mg to 15 mg, in a preferred range of approximately 1 mg to 10 mg, and in a most preferred range of approximately 2.5 mg to 7.5 mg, Quercetin in a range of approximately 50 mg to 1000 mg, in a preferred range of approximately 75 mg to 500 mg, and in a most preferred range of approximately 100 mg to 250 mg, Stinging nettles in a powder form in a range of approximately 50 mg to 1000 mg, in a preferred range of approximately 75 mg to 500 mg, and in a most preferred range of approximately 100 mg to 250 mg, Elderberry in a range of approximately 50 mg to 1000 mg, in a preferred range of approximately 75 mg to 500 mg, and in a most preferred range of approximately 100 mg to 250 mg, Goldenseal in a range of approximately 50 mg to 1000 mg, in a preferred range of approximately 75 mg to 500 mg, and in a most preferred range of approximately 100 mg to 250 mg, Curcumin in a range of approximately 50 mg to 1000 mg, in a preferred range of approximately 75 mg to 500 mg, and in a most preferred range of approximately 100 mg to 250 mg, and Ascorbic acid in a range of approximately 50 mg to 1000 mg, in a preferred range of approximately 75 mg to 500 mg, and in a most preferred range of approximately 100 mg to 250 mg, is administered to a person suffering from sinus and allergy discomfort, in the form of a tablet or capsule every 4 to 6 hours for clearing the nasal passages and relieving sinus pressure as well as providing an immune boosting effect.

EXAMPLE 7

A composition comprising Pseudoephedrine sulfate in a range of approximately 10 mg to 100 mg, in a preferred range of approximately 15 mg to 75 mg, and in a most preferred range of approximately 25 mg to 50 mg, Diphenhydramine sulfate in a range of approximately 5 mg to 50 mg, in a preferred range of approximately 10 mg to 40 mg, and in a most preferred range of approximately 15 mg to 30 mg, Quercetin in a range of approximately 50 mg to 1000 mg, in a preferred range of approximately 75 mg to 500 mg, and in a most preferred range of approximately 100 mg to 250 mg, Stinging nettles in a powder form in a range of approximately 50 mg to 1000 mg, in a preferred range of approximately 75 mg to 500 mg, and in a most preferred range of approximately 100 mg to 250 mg, Elderberry in a range of approximately 50 mg to 1000 mg, in a preferred range of approximately 75 mg to 500 mg, and in a most preferred range of approximately 100 mg to 250 mg, Goldenseal in a range of approximately 50 mg to 1000 mg, in a preferred range of approximately 75 mg to 500 mg, and in a most preferred range of approximately 100 mg to 250 mg, Curcumin in a range of approximately 50 mg to 1000 mg, in a preferred range of approximately 75 mg to 500 mg, and in a most preferred range of approximately 100 mg to 250 mg, and Ascorbic acid in a range of approximately 50 mg to 1000 mg, in a preferred range of approximately 75 mg to 500 mg, and in a most preferred range of approximately 100 mg to 250 mg, is administered to a person suffering from sinus and allergy discomfort, in the form of a liquid, tablet or capsule every 4 to 6 hours to relieve sinus pressure, clear nasal passages and provide an immune boosting effect.

EXAMPLE 8

A composition comprising Acetaminophen in a range of approximately 50 mg to 1000 mg, in a preferred range of approximately 75 mg to 750 mg, and in a most preferred range of approximately 100 mg to 650 mg, Bromelain in a range of approximately 50 mg to 1000 mg, in a preferred range of approximately 75 mg to 500 mg, and in a most preferred range of approximately 100 mg to 250 mg, Curcumin in a range of approximately 50 mg to 1000 mg, in a preferred range of approximately 75 mg to 500 mg, and in a most preferred range of approximately 100 mg to 250 mg, Ascorbic acid in a range of approximately 50 mg to 1000 mg, in a preferred range of approximately 75 mg to 750 mg, and in a most preferred range of approximately 100 mg to 500 mg, multiple pancreatic enzymes in a range of approximately 50 mg to 1000 mg, in a preferred range of approximately 75 mg to 500 mg, and in a most preferred range of approximately 100 mg to 250 mg, and primrose oil in a range of approximately 50 mg to 1000 mg, in a preferred range of approximately 75 mg to 500 mg, and in a most preferred range of approximately 100 mg to 350 mg is administered to a human in a tablet form, every 4 to 6 hours in order to bring about pain relief, promote the healing of injured tissues and provide an antioxidant effect.

EXAMPLE 9

A composition comprising Aspirin in a range of approximately 50 mg to 1000 mg, in a preferred range of approximately 100 mg to 750 mg, and in a most preferred range of approximately 250 mg to 600 mg, Bromelain in a range of approximately 50 mg to 1000 mg, in a preferred range of approximately 75 mg to 500 mg, and in a most preferred range of approximately 100 mg to 250 mg, Curcumin in a range of approximately 50 mg to 1000 mg, in a preferred range of approximately 75 mg to 500 mg, and in a most preferred range of approximately 100 mg to 250 mg, Ascorbic acid in a range of approximately 50 mg to 1000 mg, in a preferred range of approximately 75 mg to 750 mg, and in a most preferred range of approximately 100 mg to 500 mg, multiple pancreatic enzymes in a range of approximately 50 mg to 1000 mg, in a preferred range of approximately 75 mg to 500 mg, and in a most preferred range of approximately 100 mg to 250 mg, and primrose oil in a range of approximately 50 mg to 1000 mg, in a preferred range of approximately 75 mg to 500 mg, and in a most preferred range of approximately 100 mg to 350 mg is administered to a human in a tablet form, every 4 to 6 hours in order to bring about pain relief, repair injured tissues and provide and antioxidant effect.

EXAMPLE 10

A composition comprising Ibuprofen in a range of approximately 50 mg to 500 mg, in a preferred range of approximately 75 mg to 350 mg, and in a most preferred range of approximately 100 mg to 250 mg, Bromelain in a range of approximately 50 mg to 1000 mg, in a preferred range of approximately 75 mg to 500 mg, and in a most preferred range of approximately 100 mg to 250 mg, Curcumin in a range of approximately 50 mg to 1000 mg, in a preferred range of approximately 75 mg to 500 mg, and in a most preferred range of approximately 100 mg to 250 mg, Ascorbic acid in a range of approximately 50 mg to 1000 mg, in a preferred range of approximately 75 mg to 750 mg, and in a most preferred range of approximately 100 mg to 500 mg, multiple pancreatic enzymes in a range of approximately 50 mg to 1000 mg, in a preferred range of approximately 75 mg to 500 mg, and in a most preferred range of approximately 100 mg to 250 mg, and primrose oil in a range of approximately 50 mg to 1000 mg, in a preferred range of approximately 75 mg to 500 mg, and in a most preferred range of approximately 100 mg to 350 mg is administered to a human in a tablet form, every 4 to 6 hours in order to bring about pain relief and repair injured tissues.

EXAMPLE 11

A composition comprising Ibuprofen in a range of approximately 50 mg to 500 mg, in a preferred range of approximately 75 mg to 350 mg, and in a most preferred range of approximately 100 mg to 250 mg, Feverfew (*Tanacetum parthenium*) in a range of approximately 50 mg to 500 mg, in a preferred range of approximately 75 mg to 350 mg, and in a most preferred range of approximately 100 mg to 250 mg, Ginger root (*Zingiber officinale*) in a range of approximately 10 mg to 500 mg, in a preferred range of approximately 25 mg to 350 mg, and in a most preferred range of approximately 50 mg to 150 mg, Natural marine lipid concentrate in a range of approximately 500 mg to 1500 mg, in a preferred range of approximately 750 mg to 1250 mg, and in a most preferred range of approximately 950 mg to 1100 mg, Eicosapentaenoic acid in a range of approximately 50 mg to 300 mg, in a preferred range of approximately 75 mg to 250 mg, and in a most preferred range of approximately 100 mg to 200 mg, Docosahexaenoic acid in a range of approximately 50 mg to 250 mg, in a preferred range of approximately 75 mg to 200 mg, and in a most preferred range of approximately 100 mg to 150 mg, is administered to a person suffering from the effects of a migraine headache, in the form of a capsule, every 4 to 6 hours, to treat pain and relieve migraine symptoms.

EXAMPLE 12

Between 2.5 ml and 10 ml of a composition comprising Ranitidine in a range of approximately 10 mg to 200 mg, in a preferred range of approximately 25 mg to 150 mg, and in a most preferred range of approximately 50 mg to 100 mg, Ginger root in a range of approximately 50 mg to 500 mg, in a preferred range of approximately 75 mg to 350 mg, and in a most preferred range of approximately 100 mg to 300 mg, Licorice root (*Glycyrrhiza uralensis*) in a range of approximately 50 mg to 500 mg, in a preferred range of approximately 75 mg to 350 mg, and in a most preferred range of approximately 100 mg to 250 mg, aloe vera extract in a range of approximately 5 mg to 100 mg, in a preferred range of approximately 10 mg to 75 mg, and in a most preferred range of approximately 15 mg to 35 mg, L-Glutamine in a range of approximately 250 mg to 1000 mg, in a preferred range of approximately 350 mg to 750 mg, and in a most preferred range of approximately 450 mg to 550 mg, and Horseradish root in a range of approximately 50 mg to 500 mg, in a preferred range of approximately 75 mg to 350 mg, and in a most preferred range of approximately 100 mg to 250 mg, is administered to a person suffering from indigestion, in liquid form up to four times daily to serve as a histamine antagonist and reduce the symptoms of indigestion.

EXAMPLE 13

Between 5 ml and 10 ml of a composition comprising Cimetidine in a range of approximately 50 mg to 300 mg, in a preferred range of approximately 75 mg to 250 mg, and in a most preferred range of approximately 100 mg to 200 mg, Ginger root in a range of approximately 50 mg to 500 mg, in a preferred range of approximately 75 mg to 350 mg, and in a most preferred range of approximately 100 mg to 300 mg, Licorice root (*Glycyrrhiza uralensis*) in a range of approximately 50 mg to 500 mg, in a preferred range of approximately 75 mg to 350 mg, and in a most preferred range of approximately 100 mg to 250 mg, aloe vera extract in a range of approximately 5 mg to 100 mg, in a preferred range of approximately 10 mg to 75 mg, and in a most preferred range of approximately 15 mg to 35 mg, L-Glutamine in a range of approximately 250 mg to 1000 mg, in a preferred range of approximately 350 mg to 750 mg, and in a most preferred range of approximately 450 mg to 550 mg, and Horseradish root in a range of approximately 50 mg to 500 mg, in a preferred range of approximately 75 mg to 350 mg, and in a most preferred range of approximately 100 mg to 250 mg, is administered to a person suffering from indigestion, in liquid form up to four times daily to prevent gastrointestinal distress.

EXAMPLE 14

A composition comprising phenylephrine hydrochloride (1%), *Echinacea purpurea* in an approximate range of 50 mg to 500 mg, in a preferred range of approximately 100 mg to 350 mg, and in a most preferred range of approximately 150 mg to 250 mg, elderberry in an approximate range of 50 mg to 500 mg, in a preferred range of approximately 100 mg to 300 mg, and in a most preferred range of approximately 150 mg to 250 mg, Zinc gluconate in an approximate range of 2.5 mg to 30 mg, in a preferred range of approximately 5 mg to 25 mg, and in a most preferred range of approximately 10 mg to 20 mg, sodium ascorbate (1.5%) and grapefruit seed extract (0.10%), is administered to a person suffering from the symptoms of a cold and flu in the form of 2 sprays up to four times daily to prevent sinus congestion and boost the immune system.

EXAMPLE 15

A composition comprising *Echinacea purpurea* in an approximate range of 50 mg to 500 mg, in a preferred range of approximately 100 mg to 350 mg, and in a most preferred range of approximately 150 mg to 250 mg, elderberry in an approximate range of 50 mg to 500 mg, in a preferred range of approximately 100 mg to 300 mg, and in a most preferred range of approximately 150 mg to 250 mg, Zinc gluconate in an approximate range of 2.5 mg to 30 mg, in a preferred range of approximately 5 mg to 25 mg, and in a most preferred range of approximately 10 mg to 20 mg, sodium ascorbate (1.5%), grapefruit seed extract (0.10%) and sodium chloride (0.65%), is administered to a person suffering from nasal and sinus discomfort in the form of a 2 to 3 sprays up to four times daily to relieve sinus congestion and provide and immune system boost.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A pain relieving medicinal composition, consisting of:
   an effective amount of at least one non-steroidal anti-inflammatory drug;
   an effective amount of glucosamine sulfate, chondroitin sulfate, or a combination thereof;
   at least one plant extract, said plant extract being selected from the group consisting of (i) an antioxidant extract; (ii) an immune boosting extract; (iii) an extract of milk thistle in combination with at least one of (i) and (ii); and (iv) mixtures thereof; and
   a pharmaceutically acceptable medium.

2. The medicinal composition according to claim 1, wherein:
   said non-steroidal anti-inflammatory drug is selected from the group consisting of acetaminophen, dielophenac, fenflofenac, aspirin, indomethacin, sulindac, tolmetin, ibuprofen, ketoprofen, fenoprofen, flurbiprofen, naproxen, meclofenamic acid, flufenamic acid, piroxicam, tenoxicam, meloxicam, celicoxib, roficoxib, nabumetone, and combinations thereof.

3. The medicinal composition according to claim 1, wherein:
   said at least one plant extract consists of an antioxidant extract selected from the group consisting of a garlic extract, a green tea extract, an *Astragalus* extract, a grapefruit seed extract, and combinations thereof.

4. The medicinal composition according to claim 1, wherein:
   said at least one plant extract consists of an immune boosting extract selected from the group consisting of a coneflower extract, an elderberry extract, a goldenseal extract, and combinations thereof.

5. The medicinal composition according to claim 1, wherein:
   said at least one plant extract consists of an extract of milk thistle in combination with an antioxidant extract selected from the group consisting of a garlic extract, a green tea extract, an *Astragalus* extract, a grapefruit seed extract, and combinations thereof.

6. The medicinal composition according to claim 1, wherein:
   said at least one plant extract consists of an extract of milk thistle in combination with an immune boosting extract selected from the group consisting of a coneflower extract, an elderberry extract, a goldenseal extract, and combinations thereof.

7. The medicinal composition according to claim 1, wherein:
   said at least one plant extract consists of (i) an antioxidant extract; (ii) an immune boosting extract; and (iii) an extract of milk thistle;
   wherein said antioxidant extract is selected from the group consisting of a garlic extract, a green tea extract, an *Astragalus* extract, a grapefruit seed extract, and combinations thereof; and
   wherein said immune boosting extract is selected from the group consisting of a coneflower extract, an elderberry extract, a goldenseal extract, and combinations thereof.

8. The medicinal composition according to claim 1, wherein:
   said plant extract consists of from 50 to 250 mg of an antioxidant extract selected from the group consisting of a garlic extract, a green tea extract, an *Astragalus* extract, a grapefruit seed extract, and combinations thereof; and
   from 10 to 100 mg of an extract of milk thistle.

9. The medicinal composition according to claim 1, wherein:
   said plant extract consists of from 50 to 250 mg of an antioxidant extract selected from the group consisting of a coneflower extract, an elderberry extract, a goldenseal extract, and combinations thereof; and
   flow 10 to 100 mg of an extract of milk thistle.

10. A method of treating pain, comprising the step of administering a medicinal composition, said medicinal composition consisting of:
    an effective amount of at least or non-steroidal anti-inflammatory drug;
    an effective amount of glucosamine sulfate, chondroitin sulfate, or a combination thereof;
    at least one plant extract, said plant extinct being selected from the group consisting of (i) an antioxidant extract; (ii) an immune boosting extract; (iii) an extract of milk thistle in combination with at least one of (i) and (ii); and (iv) mixtures thereof; and
    a pharmaceutically acceptable medium.

11. The method according to claim 10, wherein:
    said non-steroidal anti-inflammatory drug is selected from the group consisting of acemminophen, diclophenac, fenflofenac, aspirin, indomethacin, sulindac, tolmetin ibuprofen, ketoprofen, fenoprofen, flurbiprofen, naproxen, meclofenamic acid, flufenamic acid, piroxicam, tenoxicam, meloxicam, celicoxib, roficoxib, nabumetone, and combinations thereof.

12. The method according to claim 10, wherein:
    said at least one plant extract consists of an antioxidant extract selected from the group consisting of a garlic extract, a green tea extract, an *Astragalus* extract, a grapefruit seed extract and combinations thereof.

13. The method according to claim 10, wherein:
    said at least one plant extract consists of an immune boosting extract selected from the group consisting of a coneflower extract, an elderberry extract, a goldenseal extract, and combinations thereof.

14. The method according to claim 10, wherein:
    said at least one plant extract consists of an extract of milk thistle in combination with an antioxidant extract selected from the group consisting of a garlic extract, a green tea extract, an *Astragalus* extract, a grapefruit seed extract, and combinations thereof.

15. The method according to claim 10, wherein:

said at least one plant extract consists of an extract of milk thistle in combination with an immune boosting extract selected from the group consisting of a coneflower extract, an elderberry extract a goldenseal extract, and combinations thereof.

16. The method according to claim 10, wherein:

said at least one plant extract consists of (i) an antioxidant extract; (ii) an immune boosting extract; and (iii) an extract of milk thistle;

wherein said antioxidant extract is selected from the group consisting of a garlic extract, a green tea extract, an *Astragalus* extract, a grapefruit seed extract, and combinations thereof; and wherein said immune boosting extract is selected from the group consisting of a coneflower extract, an elderberry extinct, a goldenseal extract, and combinations thereof.

17. The method according to claim 10, wherein:

said plant extract consists of from 50 to 250 mg of an antioxidant extract selected from the group consisting of a garlic extract, a green tea extract, an *Astntgalus* extract, a grapefruit seed extract, and combinations thereof; and from 10 to 100 mg of an extract of milk thistle.

18. The method according to claim 10, wherein:

said plant extract consists of from 50 to 250 mg of an antioxidant extract selected from the group consisting of a coneflower extract, an elderberry extract, a goldenseal extract, and combinations thereof; and from 10 to 100 mg of an extract of milk thistle.

* * * * *